(12) United States Patent
Bee

(10) Patent No.: US 6,233,395 B1
(45) Date of Patent: May 15, 2001

(54) METHOD FOR QUANTITATIVE IRIS COLORIMETRY

(75) Inventor: Walter H. Bee, Hamm (DE)

(73) Assignee: Covance Laboratories GmbH, Munster (DE)

( * ) Notice: Subject to any disclaimer, the term of this patent is extended or adjusted under 35 U.S.C. 154(b) by 0 days.

(21) Appl. No.: 08/934,483

(22) Filed: Sep. 19, 1997

Related U.S. Application Data

(60) Provisional application No. 60/026,375, filed on Sep. 20, 1996.

(51) Int. Cl.$^7$ ................................................ G01D 3/46
(52) U.S. Cl. ..................... 386/402; 128/745; 128/655; 356/425
(58) Field of Search ......................... 356/402; 128/745, 128/655

(56) References Cited

U.S. PATENT DOCUMENTS

| | | | |
|---|---|---|---|
| 4,411,257 | 10/1983 | Machida | 128/6 |
| 4,682,305 | * 7/1987 | Ishikawa . | |
| 5,297,554 | * 3/1994 | Glynn et al. | 128/665 |
| 5,432,863 | 7/1995 | Benati et al. | 382/167 |
| 5,495,338 | * 2/1996 | Gouriou et al. . | |
| 5,609,159 | * 3/1997 | Kandel et al. | 128/745 |

OTHER PUBLICATIONS

Bee, et al., "Computer–Assisted Evaluation of Iris Color Changes in Primate Toxicity Studies", *Advances in Ocular Toxicology*, pp. 203–205, *Plenum Press,* New York, 1997.

* cited by examiner

*Primary Examiner*—Frank G. Font
*Assistant Examiner*—Reginald A. Ratliff
(74) *Attorney, Agent, or Firm*—Dechert

(57) ABSTRACT

A method for carrying out quantitative iris colorimetry on an eye is disclosed comprising the steps of detecting the iris coloration by means for converting it into an electronic signal, quantitatively comparing said electronic signal to a provided electronic standard, and computing a quantitative value representative of the iris coloration. The preferred means for converting it into a signal is a is a video camera and the preferred storage means is a computer memory, either in a magnetic or optical disk.

13 Claims, 7 Drawing Sheets

(2 of 7 Drawing Sheet(s) Filed in Color)

FIG. 4A
FIG. 4B
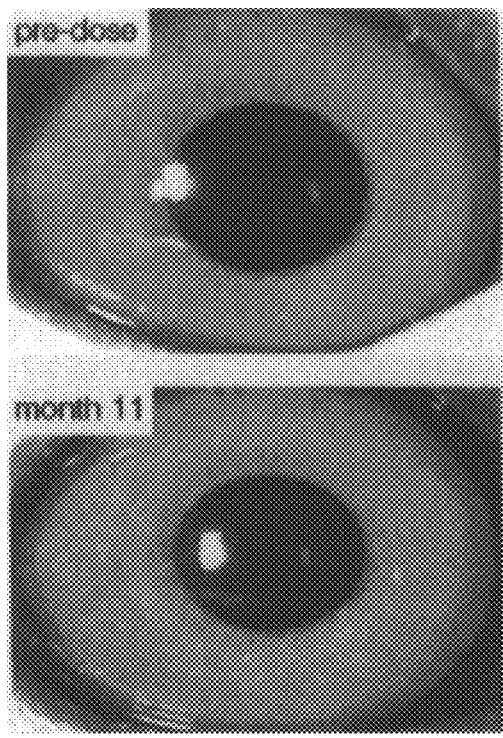
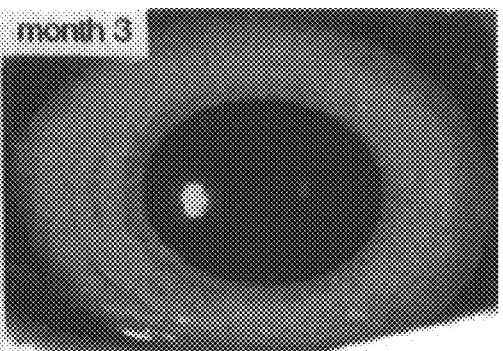
Figure 4: Sample pictures for a Rescula treated eye;
pre-dose - R+G+B=486
month 3 - R+G+B=440
month 11 - R+G+B=487
FIG. 4C

METHOD FOR QUANTITATIVE IRIS COLORIMETRY

RELATED APPLICATIONS

This application claims benefit of U.S. Provisional Application No. 60/026,375, filed Sep. 20, 1996.

BACKGROUND OF THE INVENTION

This invention relates to a method of quantitatively measuring and monitoring color values and changes in the iris of an eye. Iris coloration may be affected by many factors—some related to disease or to administered medications, especially those useful for conditions of the eye. For example, members of the class of pharmaceutical compositions known as prostaglandins have known therapeutic activity in reducing intraocular pressure and are, therefore, regarded as a promising medication for glaucoma. One example is the prostaglandin known commonly as latanoprost (isopropyl-(Z)-7[(1R,2R,3R,5S)3,5-dihydroxy-2-[(3R)-3-hydroxy-5-phenylpentyl]cyclo-pentyl]-5-heptenoate), which is commercially available from Pharmacia & Upjohn under the trademark XALATAN™. It is generally well-tolerated, systemically and in the eye. However, one side effect of administration of this prostaglandin compound, especially in larger primates and man, is increased pigmentation of the iris of the eye. This effect was found, for example, in about 5% to 15% of Cynomolgus monkeys in multi-center clinical trials.

This effect appears mainly in mixed color eyes such as blue-brown, green-brown, yellow-brown, and grey-brown, and may result in a darker iris. The effect has not been noted in dark-brown irises. The first changes in pigmentation generally occur after three months of prostaglandin treatment. In monkeys with yellow-green eyes, a dose-dependent increase in pigmentation was noted after 3–12 months of topical prostaglandin administration. This side effect may be cosmetically undesirable, and may be indicative of other concerns relating to therapeutic treatment of a patient to whom such iris color-effecting medications are administered.

The long-term effect and the mechanism for this adverse reaction are not entirely known. Some studies have indicated that stimulation of melanin production, rather than proliferation of melanocytes may be a cause. While it is not known if all prostaglandins exhibit this effect, another example currently being tested is isopropyl unoprostone, marketed under the trade name RESCULA®.

We have discovered that iris coloration can be quantitatively determined so that changes in iris coloration can be monitored quantitatively over time. Hence, in the case of naturally- or drug-induced iris color changes, the progress of the causative condition or therapy can be correspondingly monitored. The method has applicability in pharmacology and toxicology as well as in the monitoring of patients treated with anti-glaucoma medications.

It is known conventionally to compare iris color to a known standard color scale by visual observation of the iris side-by-side with the standard (which can be incorporated into the photograph). However, it is generally necessary to record the iris coloration by photograph; and color changes in photographs over time, as well as differences in development chemistry from film sample to film sample, make difficult if not impossible the reliable long-term monitoring of the same iris. Such changes in development, for example, ordinarily require that each photograph be developed manually and calibrated to a color scale which must be included on the photograph along with the object.

Hence, such methodology is generally expensive, complicated, time-consuming and unreliable. Further, the visual observer's perceptive eyesight is inherently problematic and the results necessarily subjective. Even discounting these natural handicaps, evaluation of approximate eye color by comparison against a standard color scale cannot be more than a rough visual integration of the average pigmentation of the evaluation area.

SUMMARY OF THE INVENTION

A method for carrying out quantitative iris colorimetry on an eye is disclosed, comprising the steps of detecting the iris coloration by means for converting it into an electronic signal, quantitatively comparing said electronic signal to a provided electronic standard, and computing a quantitative value representative of the iris coloration. The preferred means for converting it into a signal is a is a video camera and the preferred storage means is a computer memory, either in a magnetic or optical disk.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 4A–C illustrates color changes in a selected monkey from the RESCULA® treatment experiment over time.

DETAILED DESCRIPTION OF THE INVENTION

Figure 1:
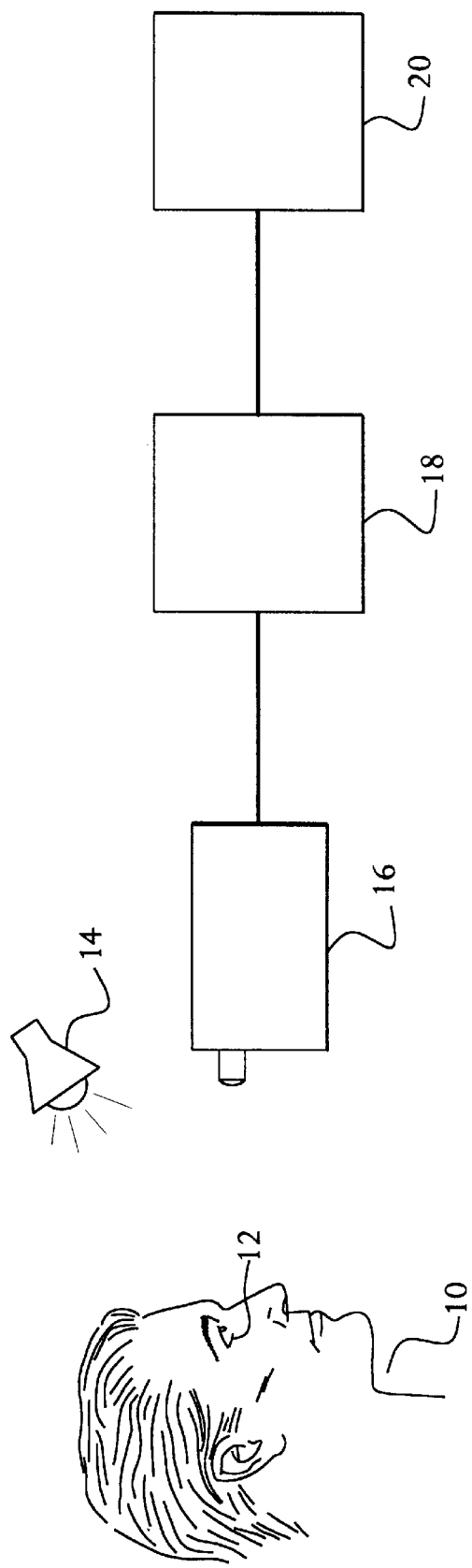
FIG. 1 is a schematic of an experimental set-up of the present invention.

According to the invention, the iris coloration of the subject eye is detected by a means for converting it into an electronic signal. As shown schematically in FIG. 1, 10 represents an animal, preferably a heavier primate or a human, having an eye 12. The electronic conversion means, 16, preferably comprises a video camera. Another means would include a digital still camera having color calibration capability. A suitable device, 14, for illuminating and magnifying the iris of the eye 12, (e.g., an ophthalmologic slit lamp, as commercially available for example from Zeiss), is directed toward the iris surface and optically interposed between the iris and the camera 16. Preferably, the detected image is confined to the pigmented iris.

Figure 2:
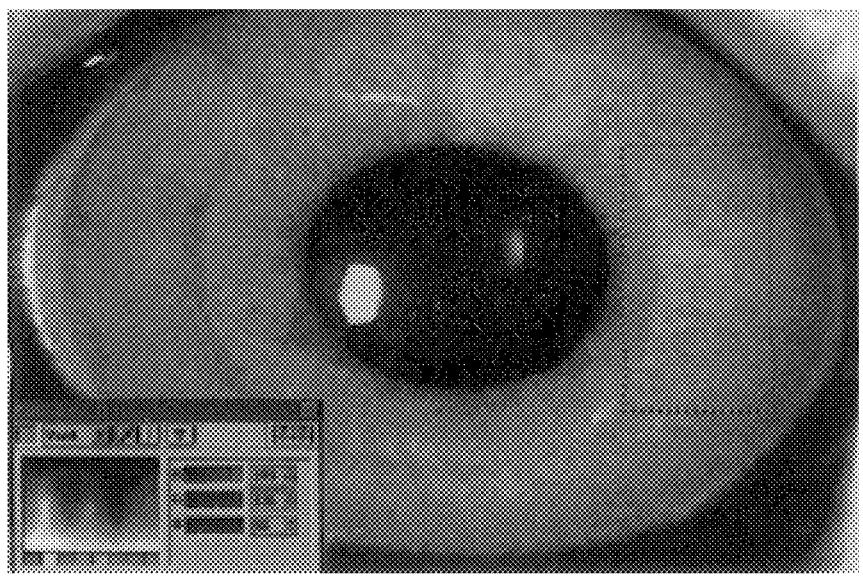
FIG. 2 depicts color analysis of and iris; values are separately given for red, green, and blue components, each numerically ranging from 0 (minimum) to 255 (maximum).
Figure 3A:
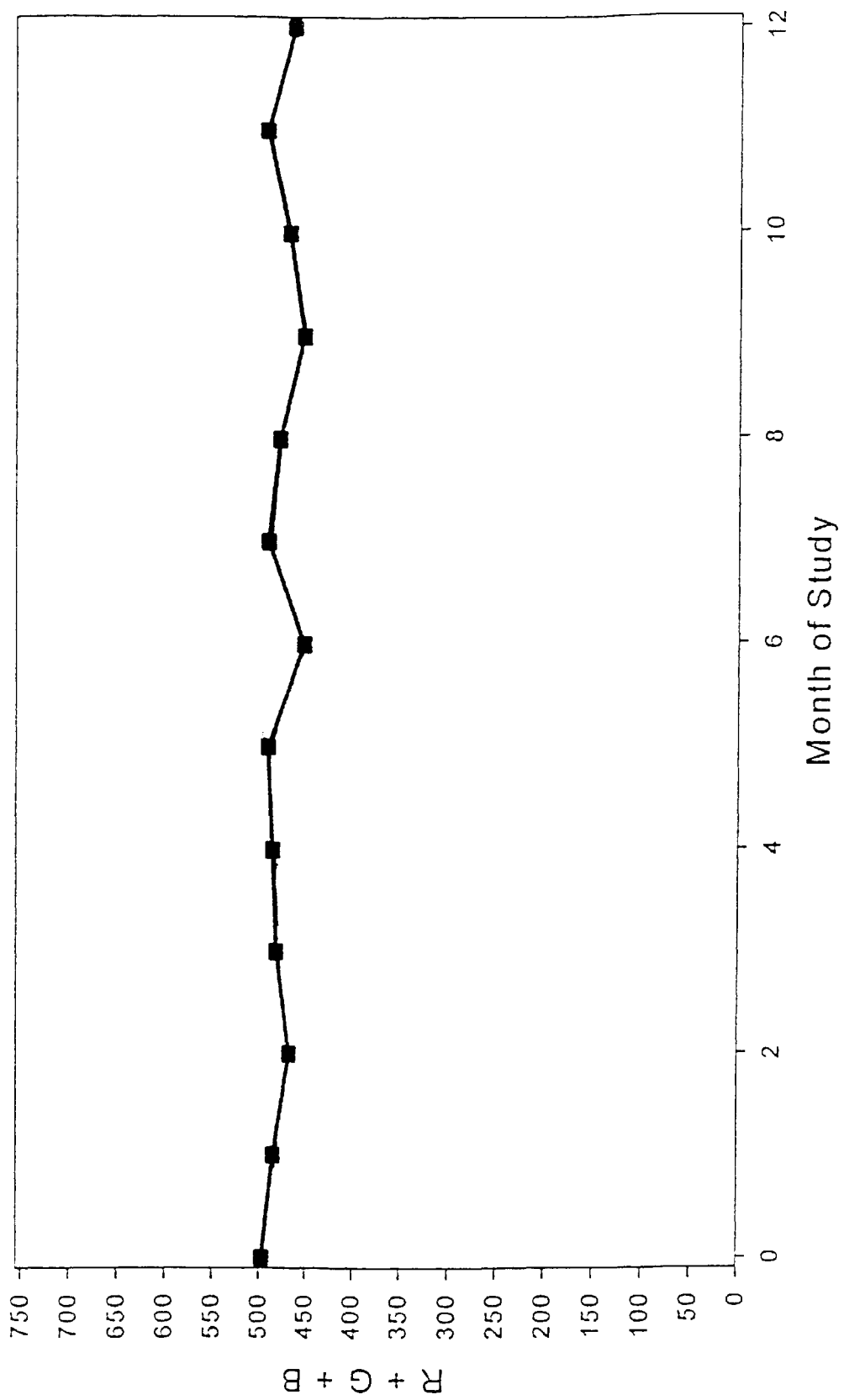
FIG. 3A is a graph of time dependent intensity recording of the iris color in an untreated control group of Cynomolgus monkeys.
Figure 3B:
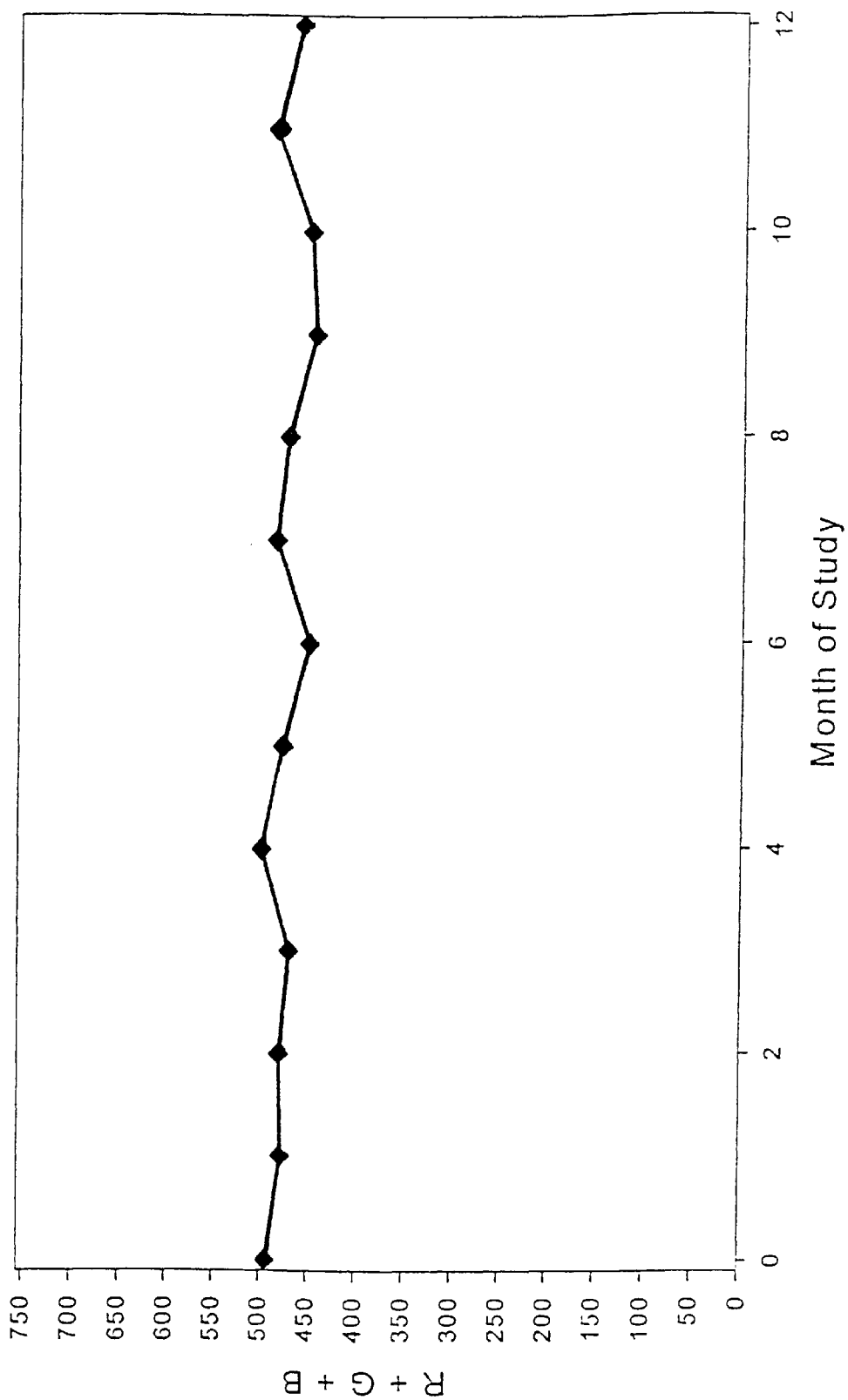
FIG. 3B is a graph of time dependent intensity recording of the iris color in a treated control group of Cynomolgus monkeys.
Figure 3C:
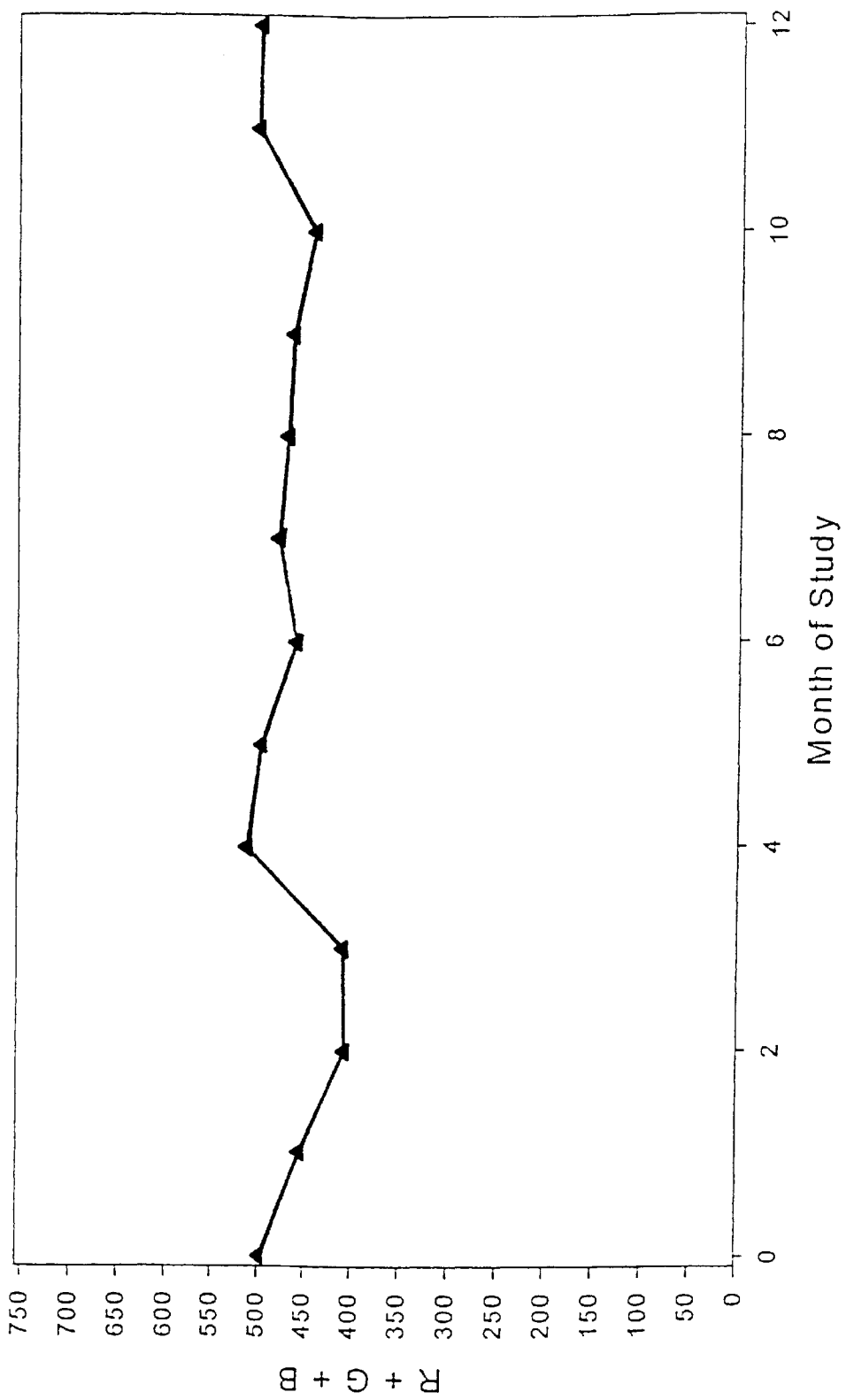
FIG. 3C is a graph of time dependent intensity recording of the iris color in a treated dose group of Cynomolgus monkeys.
Figure 3D:
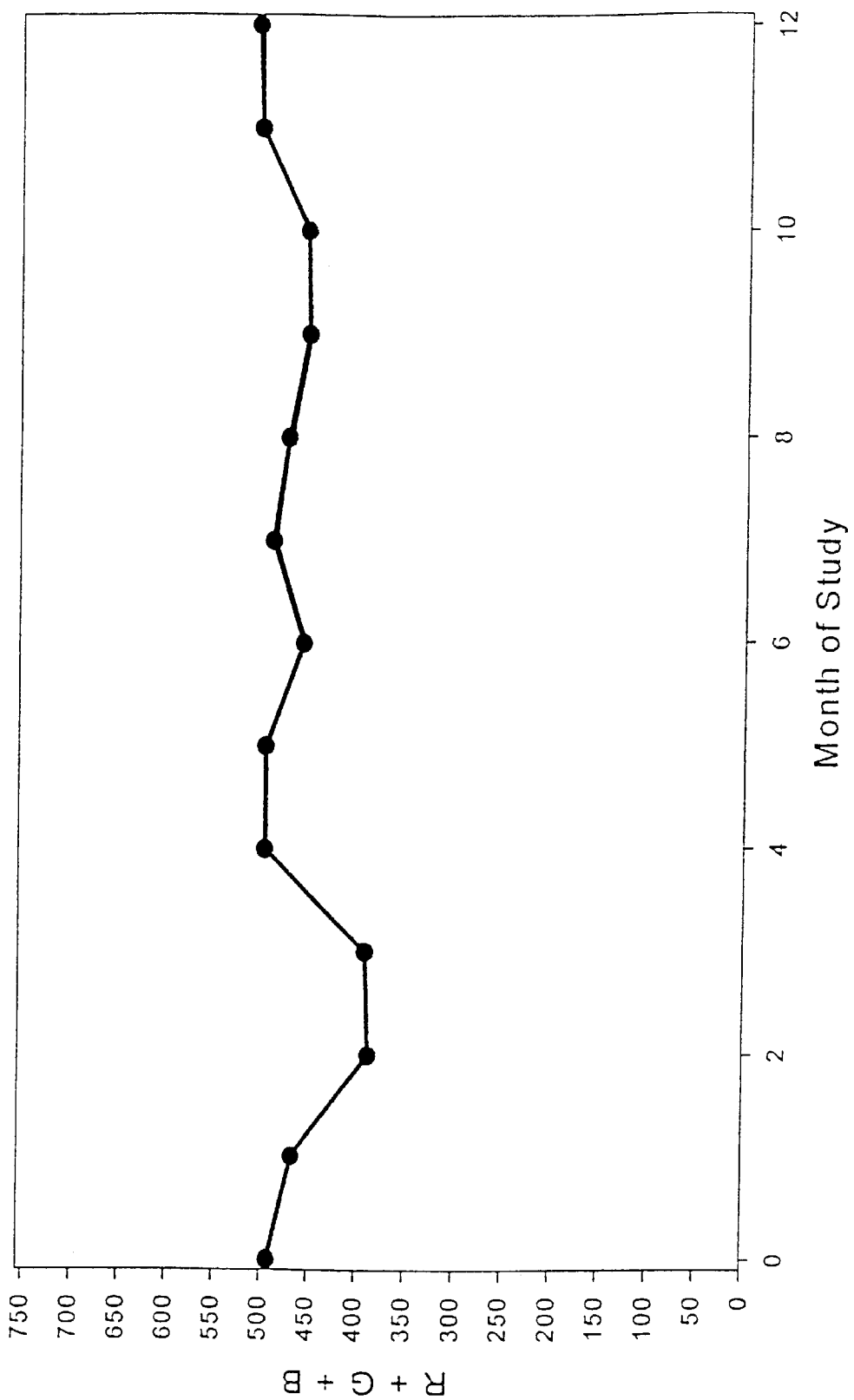
FIG. 3D is a graph of time dependent intensity recording of the iris color in an untreated dose group of Cynomolgus monkeys.

As shown in FIG. 2, a rectangular region of the iris (shown by dotted lines) is selected and the electronic image is confined to such region. Since the light from the slit lamp impinges on the subject's face, creating reflection potential, the portion of the iris which is between a pupil and the nose is the preferred region to study. Preferably, a three-chip video camera (resolution e.g., 380,000 pixels) is used.

The detected color image is stored electronically, preferably in a computer memory, 18. The image may also be viewed simultaneously on a video monitor, 20. The electronic images may also be permanently stored as raw data on an optical disc or the like, or they can be converted to compressed format and stored on a magnetic disc. A single scanned image of the subject iris is selected, e.g. by a "grabber card" (e.g., that which is part of the Movie Software, Fast Movie Machine II, available commercially from FAST) in the computer. The video camera 16 (color, brightness, contrast), illuminating means, 14, such as slit lamp (intensity—exposure meter) and computer 18, (standard color recordation using Pantone color scales) are all calibrated for accuracy and reproducibility in advance of taking the data. Alternatively, a series of images could be electronically averaged together.

Conventional image-analysis software (e.g., photo design software such AS PHOTO STYLER® or PHOTO SHOP® available commercially from Adobe) capable of quantitative colorimetry is then used to analyze the scanned image. Preferably, the average color numerical value as well as the red, green and blue derivative values of the overall averaged scanned image are displayed and recorded by the computer. Repeated measurements of the same iris of a monkey generally led to a coefficient of variation of less than 3%; no human eye would be likely to detect such subtle variations. Preferably, about 10 images of the same eye are measured and the results averaged.

EXAMPLE

Groups of ten Cynomolgus monkeys were treated twice daily with isopropyl unoprostone (marketed under the trade name RESCULA®) and saline solution over 4 months. The results of twice-daily treatment are depicted in FIGS. 3A–D. While the overall intensity (red+green+blue) of the untreated eye in each monkey remained stable over the observation period, a slight transient response of the saline-treated irises was apparently, sample pictures of these are depicted in FIGS. 4A–C.

In conclusion, this computer-assisted method for iris colorimetry determination provides a fast and accurate means of measuring color changes in the irises of a subject's eyes. Although the trials reported above were carried out on monkeys, since the source of the data is optical recordation by a video camera the method is equally applicable to humans.

What is claimed is:

1. A method for performing quantitative iris colorimetry on an eye, comprising the steps of:
   a) detecting the iris coloration by means for converting it into an electronic signal;
   b) quantitatively comparing said electronic signal to a provided electronic standard;
   c) computing a quantitative value representative of the iris coloration;
   d) repeating steps a–c thereby computing at least a first quantitative value representative of the iris coloration at a first time and a second quantitative value representative of the iris coloration at a second time; and
   e) comparing the first and second quantitative values thereby quantifying a differential change in iris coloration occurring between said first and second times.

2. The method of claim 1 in which the means for converting is a video camera.

3. The method of claim 1 in which the electronic signal is stored in a computer memory.

4. The method of claim 1 in which the electronic standard is stored in a computer memory.

5. The method of claim 1 in which the quantitative value is numerically displayed to the method user.

6. The method of claim 3 or 4 in which the computer memory is a magnetic disk.

7. The method of claim 3 or 4 in which the computer memory is an optical disk.

8. A method for performing quantitative iris colorimetry on an eye, comprising the steps of:
   a) converting iris coloration into an electronic signal,
   b) quantitatively comparing said electronic signal to an electronic standard; and,
   c) computing a quantitative value representative of the iris coloration; wherein the iris coloration is converted into an electronic signal using a video camera
   d) repeating steps a–c thereby computing at least a first quantitative value representative of the iris coloration at a first time and a second quantitative value representative of the iris coloration at a second time; and
   e) comparing the first and second quantitative values thereby quantifying a differential change in iris coloration occurring between said first and second times.

9. The method of claim 8, wherein the electronic signal is stored in a computer memory.

10. The method of claim 8, wherein the electronic standard is stored in a computer memory.

11. The method of claim 8, wherein the quantitative value is numerically displayed.

12. The method of claim 9, wherein the computer memory comprises at least one of a magnetic disk and an optical disk.

13. The method of claim 10, wherein the computer memory comprises at least one of a magnetic disk and an optical disk.

* * * * *